(12) United States Patent
Graichen et al.

(10) Patent No.: US 8,103,477 B2
(45) Date of Patent: Jan. 24, 2012

(54) SYSTEM AND METHOD FOR MEASURING AND REPORTING CHANGES IN WALKING SPEED

(75) Inventors: Catherine Mary Graichen, Malta, NY (US); Paul Edward Cuddihy, Ballston Lake, NY (US); Meena Ganesh, Clifton Park, NY (US); Jenny Marie Weisenberg, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 238 days.

(21) Appl. No.: 12/431,239

(22) Filed: Apr. 28, 2009

(65) Prior Publication Data
US 2009/0254004 A1  Oct. 8, 2009

Related U.S. Application Data

(62) Division of application No. 10/938,780, filed on Sep. 10, 2004, now Pat. No. 7,535,368.

(51) Int. Cl.
*G08B 23/00* (2006.01)
(52) U.S. Cl. ........................................ 702/160
(58) Field of Classification Search .................. 702/160
See application file for complete search history.

(56) References Cited

U.S. PATENT DOCUMENTS

| | | | |
|---|---|---|---|
| 6,130,858 A | 10/2000 | Felesky | |
| 6,513,381 B2 | 2/2003 | Fyfe et al. | |
| 6,524,239 B1 | 2/2003 | Reed et al. | |
| 6,816,603 B2 | 11/2004 | David et al. | |
| 6,819,247 B2 | 11/2004 | Birnbach et al. | |
| 6,954,148 B2 | 10/2005 | Pulkkinen et al. | |
| 2001/0021801 A1 | 9/2001 | Bardy | |
| 2002/0013717 A1 | 1/2002 | Ando et al. | |
| 2002/0165733 A1 | 11/2002 | Pulkkinen et al. | |
| 2003/0009308 A1 | 1/2003 | Kirtley | |
| 2003/0139692 A1 | 7/2003 | Barrey et al. | |
| 2003/0146835 A1* | 8/2003 | Carter | 340/539.13 |
| 2004/0044493 A1* | 3/2004 | Coulthard | 702/122 |

* cited by examiner

*Primary Examiner* — Cindy Hien-Dieu Khuu
(74) *Attorney, Agent, or Firm* — Marie-Claire Maple

(57) ABSTRACT

A system and method for identifying a change in walking speed of a person is provided. The system comprises a plurality of sensors disposed in various rooms of a structure. The system may also include a processor-based system that may receive signals representative of the motion and/or location of the person from the sensors. The system may establish and store a travel time for a path traveled by the person through the structure based on the signals representative of the motion and/or location of the person. The system may identify at least one path from among various travel paths traveled by the person through the structure as having a consistent travel time over a period of time. The system also identifies a change in the person's walking speed by identifying changes in the travel time for the at least one path traveled by the person through the structure.

13 Claims, 7 Drawing Sheets

| SL NO. | SENSOR TRIGGERING SEQUENCE | DURATION | FREQUENCY |
|---|---|---|---|
| 1 | 1-2-5-6-9-11-7-... | 5:20 min | 3 TIMES / MONTH |
| | | 5:18 min | |
| | | 5:21 min | |
| 2 | 1-2-3-4-5-7-8-9-... | 7:05 min | 35 TIMES / MONTH |
| | | 7:04 min | |
| | | 7:08 min | |
| | | 7:09 min | |
| | | 7:05 min | |
| | | 7:04 min | |
| | | 7:03 min | |
| | | 7:06 min | |
| | | 7:07 min | |
| | | 7:04 min | |
| | | 7:08 min | |
| | | 7:10 min | |
| | | 7:03 min | |
| | | 7:04 min | |
| | | 7:02 min | |
| | | 7:06 min | |
| | | 7:05 min | |
| | | 7:04 min | |
| | | 7:08 min | |
| | | 7:09 min | |
| | | 7:05 min | |
| | | 7:04 min | |
| | | 7:03 min | |
| | | 7:06 min | |
| | | 7:07 min | |

FIG.4

| SL NO. | SENSOR TRIGGERING SEQUENCE | DURATION | FREQUENCY |
|---|---|---|---|
| 2 | 1-2-3-4-5-7-8-9-... | 7:04 min | 35 TIMES / MONTH |
| | | 7:08 min | |
| | | 7:10 min | |
| | | 7:03 min | |
| | | 7:04 min | |
| | | 7:02 min | |
| | | 7:04 min | |
| | | 7:05 min | |
| | | 7:02 min | |
| | | 7:06 min | |
| 3 | 1-3-7-9-10-11-... | 9:16 min | 22 TIMES / MONTH |
| | | 9:12 min | |
| | | 9:15 min | |
| | | 9:06 min | |
| | | 17:06 min | |
| | | 9:17 min | |
| | | 9:16 min | |
| | | 9:22 min | |
| | | 9:17 min | |
| | | 9:14 min | |
| | | 9:16 min | |
| | | 9:12 min | |
| | | 9:15 min | |
| | | 9:16 min | |
| | | 9:06 min | |
| | | 9:18 min | |
| | | 9:15 min | |
| | | 9:13 min | |
| | | 9:17 min | |
| | | 9:12 min | |
| | | 9:15 min | |
| | | 9:16 min | |

FIG.5

| SL NO. | SENSOR TRIGGERING SEQUENCE | DURATION | FREQUENCY |
|---|---|---|---|
| 4 | 2-4-5-7-... | 3:16 min | 26 TIMES / MONTH |
| | | 3:10 min | |
| | | 7:12 min | |
| | | 3:10 min | |
| | | 3:19 min | |
| | | 8:10 min | |
| | | 5:14 min | |
| | | 3:10 min | |
| | | 3:21 min | |
| | | 3:14 min | |
| | | 6:12 min | |
| | | 3:14 min | |
| | | 3:19 min | |
| | | 8:22 min | |
| | | 5:16 min | |
| | | 3:02 min | |
| | | 2:46 min | |
| | | 3:10 min | |
| | | 8:52 min | |
| | | 10:10 min | |
| | | 3:29 min | |
| | | 4:13 min | |
| | | 5:14 min | |
| | | 7:10 min | |
| | | 3:19 min | |
| | | 3:25 min | |

SYSTEM AND METHOD FOR MEASURING AND REPORTING CHANGES IN WALKING SPEED

CROSS-REFERENCE TO RELATED APPLICATIONS

This application is a divisional of application Ser. No. 10/938,780, now granted U.S. Pat. No. 7,535,368, filed Sep. 10, 2004, entitled SYSTEM AND METHOD FOR MEASURING AND REPORTING CHANGES IN WALKING SPEED.

BACKGROUND

The invention relates generally to health monitoring systems and more particularly to a system and method for monitoring a person's walking speed over time to identify changes in walking speed.

Many elderly people live alone. The elderly also are at risk from disease and illness. Unfortunately, the elderly may not seek medical attention in a timely manner because they live alone. Worse, they may become incapacitated and not be able to call for help. In addition, the effects of illness or aging may progress slowly. Thus, an ill or aging person may not fully recognize that they are in a declining state of health. Furthermore, others with regular contact with the elderly person may not recognize the effects of illness or aging, as its progression may be too slow to be noticed.

Among other symptoms, a person may begin walking slower as their health declines or when they become ill. Similarly, a person recovering from an illness may begin walking faster as their health improves. Thus, a person's walking speed may be used as an indicator of health. Previous attempts to use a person's walking speed as a diagnostic tool have taken place in laboratory environments or in other environments outside the person's home. For example, a treadmill in a doctor's office may be used to measure a person's walking speed. However, performing the walking speed tests in these environments may introduce factors that tend to make the results of the test less informative. For example, a person's performance may be affected by being aware that the test is being performed, e.g., a patient may walk faster than normal in an attempt to do well on the test. In addition, the person has to leave their home to perform the test, which the person may not want to do.

Thus, a technique for unobtrusively measuring and monitoring the true walking speed of an individual is desirable.

SUMMARY

According to one aspect of the present technique, a system and method for identifying a change in walking speed of a person is provided. The system comprises a plurality of sensors disposed in various rooms of a structure. The sensors are operable to provide a signal representative of motion and/or the location of the person within the structure. The system may also include a processor-based system that may receive signals representative of the motion and/or location of the person from the sensors. The processor-based system may establish a travel time for a path traveled by the person through the structure based on the signals representative of the motion and/or location of the person and may store the travel time within the processor-based system. The processor-based system may identify at least one path traveled by the person through the structure from among various travel paths traveled by the person through the structure as having a consistent travel time over a period of time. The processor-based system also identifies a change in the person's walking speed by identifying changes in the travel time for the at least one path traveled by the person through the structure. The system may alert the person or a caregiver to inform them of the change in walking speed identified by the system.

The present technique also includes a system and method for operating a monitoring system to identify a change in a person's walking speed. The method may comprise receiving data representative of movement of the person within a building and the time that the movement occurred. The method may also comprise processing the data to establish a representative travel time for the person to walk along a specific sequence of sensors from among different sequences of sensors. In addition, the method may also comprise periodically comparing a current travel time for the person to walk along the specific sequence of sensors to the representative travel time to identify a changing trend in the travel time for the person to walk along the specific sequence of sensors. If there is a trend that the travel time is changing, the person's walking speed is changing over time. The system then may alert the person or a caregiver that it appears that the person's walking speed is changing and/or that medical attention may be required.

BRIEF DESCRIPTION OF THE DRAWINGS

These and other features, aspects, and advantages of embodiments of the invention will become better understood when the following detailed description is read with reference to the accompanying drawings in which like characters represent like parts throughout the drawings, wherein:

FIG. 4 is a table illustrating an exemplary set of travel duration data stored in the database, in accordance with one aspect of the present technique;

FIG. 5 is a continuation of the table illustrated in FIG. 4;

FIG. 6 is a continuation of the table illustrated in FIG. 5; and

DETAILED DESCRIPTION OF EXEMPLARY EMBODIMENTS

In the subsequent paragraphs, various aspects of a technique for unobtrusively measuring the walking speed of a person in their own home and for identifying a change in the person's walking speed will be explained.

Figure 1:
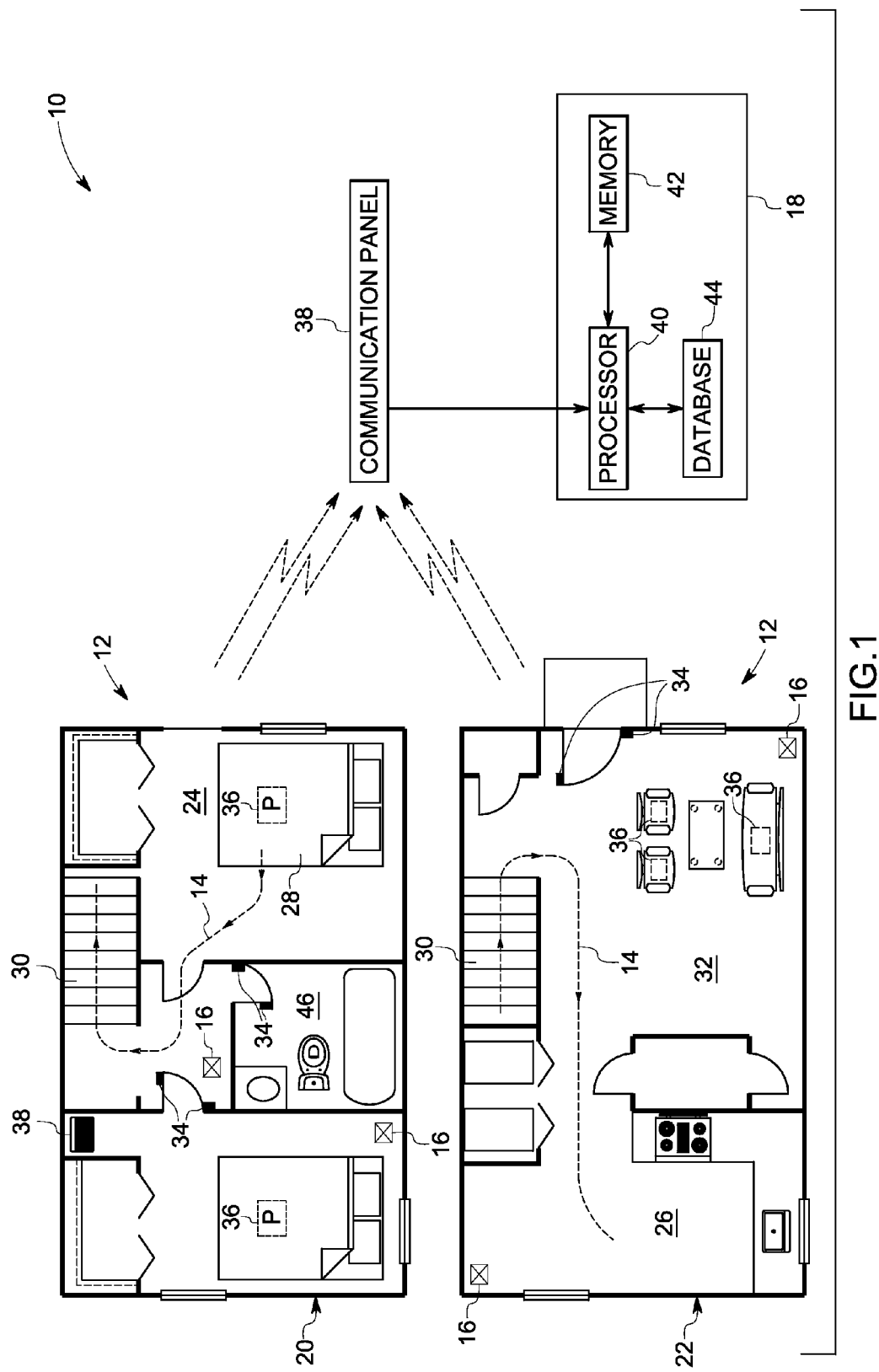
FIG. 1 is a diagrammatic view of a walking speed measurement system located at a resident's home, illustrating a typical path taken by the resident and data collected by sensors being transferred to a monitoring center, in accordance with one aspect of the present technique.

Referring generally to FIG. 1, a diagrammatic view of a walking speed measurement system 10 installed within a resident's home 12 is illustrated. The system 10 is unobtrusive and monitors the resident's walking speed through the home 12. In this view, an exemplary path that may be taken by the resident is shown, and is represented generally by reference numeral 14. The walking speed measurement system 10 comprises sensors 16 that are placed at various locations within the resident's home 12. It may be noted that a plurality of sensors may be placed in the home 12 to provide a better resolution of the walking speed and/or various paths 14 undertaken by the resident. The sensors 16 are designed to detect the resident's movements and/or actions. For example, the sensors may include motion sensors, door switches, and occupancy sensors. In addition, the sensors are designed to produce a signal when one of these events is detected.

Signals produced by the sensors 16 are transferred to a monitoring center 18. The data provided by the sensors 16 may be used by the monitoring center 18 to determine whether the resident's walking speed is changing. It may be noted that a resident may take many paths 14 through the home 12. Furthermore, the resident may stop along the way, thus making that trip not representative of the walking speed of the resident. As will be discussed in greater detail below, the system 10 is operable to identify one or more paths 14 that the resident travels through the home 12 that take a consistent duration to complete. The monitoring center 18 then monitors the duration that it takes the resident to walk each path 14 over a length of time as an indicator of the resident's walking speed over time. If the duration increases over time, it is an indication that the resident's walking speed has decreased. Similarly, if the duration decreases over time, it is an indication that the resident's walking speed has increased. The monitoring center 18 may then contact a caregiver to inform the caregiver of the change in the walking speed of the resident. If the duration remains constant, it is an indication that the resident's walking speed has not changed. The monitoring center 18 may be programmed to monitor the time that it takes the resident to walk each path 14 over the course of a single day, several days, or longer.

In one embodiment, the illustrated home 12 has two floors: a top floor 20 and a bottom floor 22. It should be appreciated that the system 10 can be installed in a home having a single floor or more than two floors or in a residential or commercial building. The illustrated path 14 of the resident extends from a master bedroom 24 on the top floor 20 to a kitchen 26 on the ground floor 22. In the illustrated path 14, the resident travels from a bed 28 in the master bedroom 24 down a staircase 30 to the kitchen 26 via a living room 32. As the resident walks along the path 14, various sensors are triggered and send signals to the monitoring center 18.

In addition to the illustrated path 14 of the resident, there may be many other paths that may be taken by the resident. The plurality of sensors 16 may be deployed within the resident's home to cover most or all of the possible travel paths 14 that the resident may take through the home 12. In this embodiment, the sensors 16 include motion sensors deployed in various rooms in the home 12, and door switches 34 that may be disposed on room doors, refrigerator doors, drawers, cabinets, etc. In addition, the plurality of sensors may include a pressure pad 36 that may be disposed on a bed or a chair to inform the monitoring center 18 when the resident is lying in bed or sitting in the chair, as well as providing an indication when the resident gets up. It may however be noted that the type of sensor used may not limit the scope of implementation of the present technique, so that any other type of sensor that can achieve similar results may be employed, as will be appreciated by one skilled in the art. For example, the pressure pad sensor 36 may be one embodiment of a sensor for detecting occupancy of the resident on beds, chairs, couches, or other seating locations. Another sensor that may be used is an infrared sensor, which is configured to detect occupancy of the beds, chairs, couches, etc. unobtrusively. In this embodiment, the sensors 16, 34, and 36 that are deployed throughout the resident's home are in wireless communication with a communication panel 38. However, the sensors may also be wired to the communication panel 38. The communication panel 38 is, in turn coupled to the monitoring center 18, such as by a telephone line, cable, or the Internet.

The illustrated monitoring center 18 has a processor 40 that is in communication with a memory 42, which stores computer readable programming instructions for directing the operation of the processor 40. The processor 40 is in communication with a database 44 that stores sensor data received from the plurality of sensors 16, 34, and 36 such as the sensor providing the signal of movement and the time that the signal was provided. The programming instructions stored in memory 42 also direct the processor 40 to determine the period of time between triggering events from different sensors. For example, the processor 40 may be programmed to establish the time between when the motion sensor 16 upstairs stopped sensing the resident's movement and when the motion detector 16 in the kitchen 26 first detected motion in the kitchen 26. This is just one example of the established path. The processor 40 is also programmed to establish the time period between triggering events detected by other sensors along the way, such as motion detected by a motion sensor 16 located in the living room 32.

The processor 40 is programmed to identify one or more paths 14 through the home that have consistent durations of time to complete. It may be noted that paths 14 where the duration is not consistent are likely to be those where the resident performs additional activities, such as, for example, stopping to comb hair, stopping to pick something up, etc. Here, a path 14 is defined as travel by the resident through the home 12 that triggers more than one sensor 16. For example, another path 14 through the home 12 may be from the kitchen 26 to an upstairs bathroom 46. The duration of the path 14 may begin when the motion sensor 16 in the kitchen 26 ceases to send a signal indicative of movement of the resident in the kitchen 26 and the path 14 may end when the resident opens the door to the bathroom 46, triggering the door switch 34. The processor 40 may also be programmed to look at a 14 path for a certain portion of the day to identify the path that has the most consistent duration.

Figure 2:
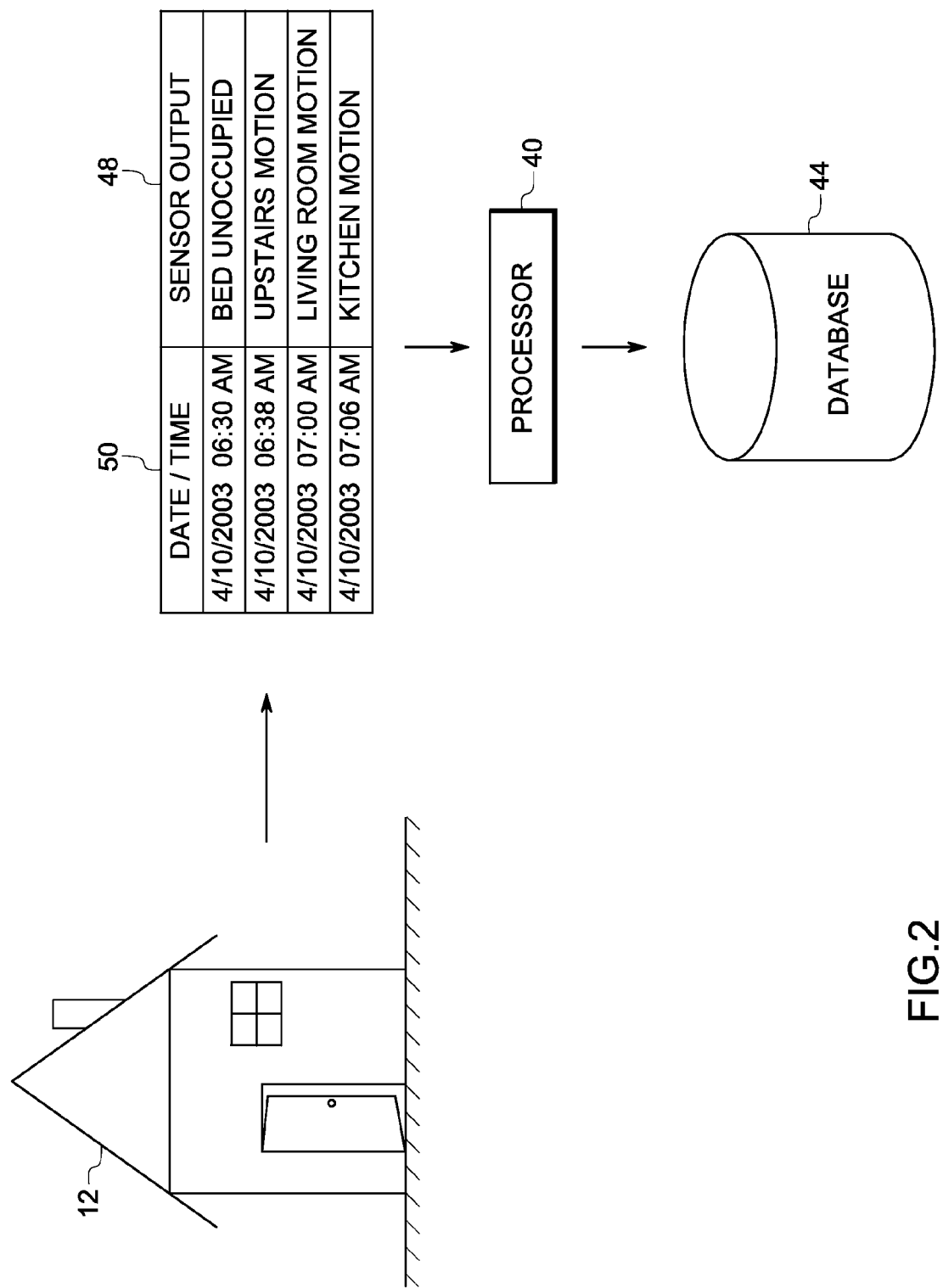
FIG. 2 is a diagrammatic view illustrating the transmission of one exemplary type of sensor data from the resident's home to the monitoring center, in accordance with one aspect of the present technique.

Referring generally to FIG. 2, a diagrammatic view of the transfer of data from the plurality of sensors 16, 34 and 36 in the home 12 to the monitoring center 18 is illustrated. As noted above, the data 48 from the sensors 16, 34 and 36 comprises the specific sensor providing the data and the action indicated by the sensor. In addition, the monitoring center 18 records the date and time 50 that the data 48 from the sensors was received. Alternatively, the date and time 50 of the event may be captured more accurately by the sensor or other related equipment disposed within the home. The higher the accuracy with which the time of the event is captured, the lower the variance caused due to any external influence such as the delay in sensor data communication or communication latency. Accordingly, communication latency will not affect the analysis of sensor data in such a case.

The data 48 and 50 is used by the processor 40 to identify the path 14 between a plurality of sensors 16, 34, and 36 that have consistent durations, or travel times. In the example provided in FIG. 2, at 6:30 a.m. on Apr. 10, 2003, the pressure pad sensor 36 disposed on the mattress of the bed 28 in the master bedroom 24 provides a signal to indicate that the resident has gotten out of bed 28. At about 6:38 a.m., the motion sensor 16 upstairs provides a signal that there is motion upstairs, indicating that the resident has left the bedroom 24 and is moving around upstairs. Next, at 7:00 a.m., the motion sensor 16 in the living room 32 provides a signal that it has detected motion in the living room 32. Finally, the motion sensor 16 installed in the kitchen 26 provides a signal to indicate that it has detected motion in the kitchen 26 at 7:06 a.m. For the purposes of evaluating the walking speed of the resident there are actually several paths represented by this data that may be considered. For example, walking from the bed 28 to the kitchen 26 represents one path. Similarly, if the resident walks from the kitchen 26 to the bedroom 24, that would indicate another path, since the sequence of triggering the sensors defines a travel path.

Figure 3:
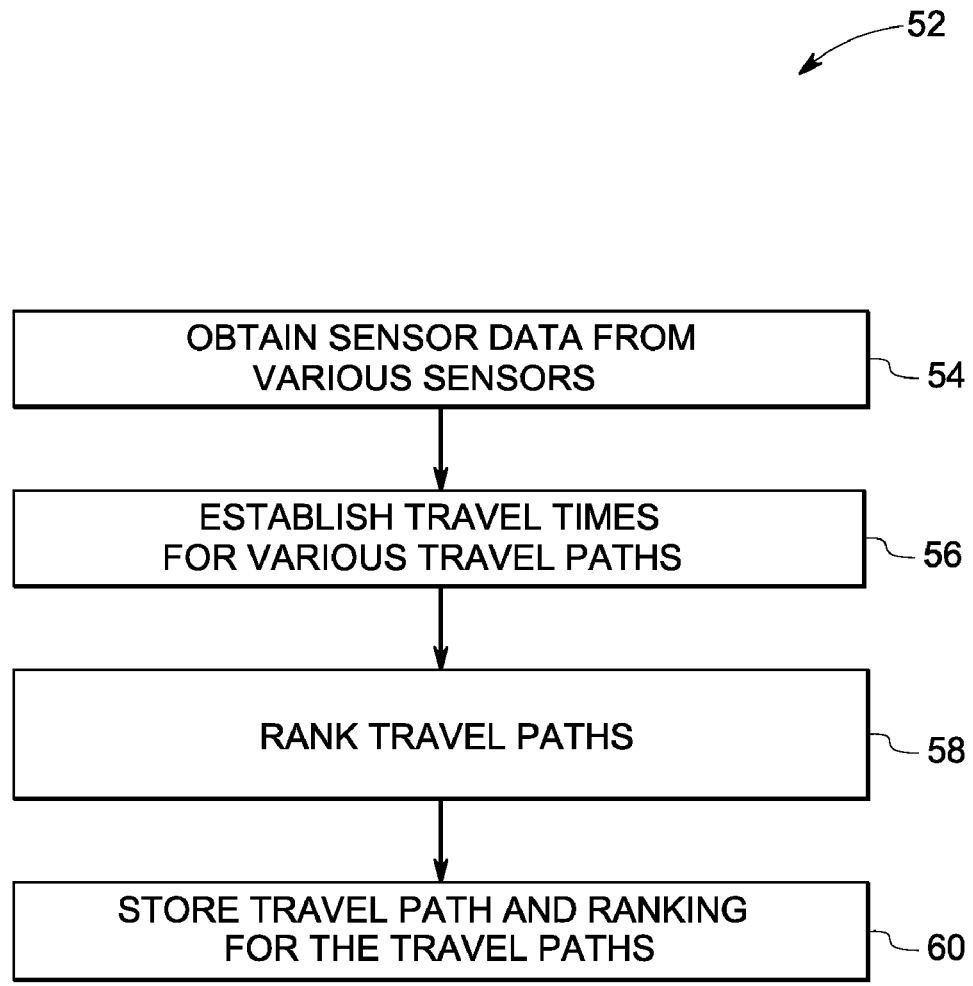
FIG. 3 is a flow chart illustrating an exemplary method for establishing a travel pattern and updating the database, in accordance with one aspect of the present technique.

Referring generally to FIG. 3, the monitoring center 18 is programmed to identify paths within the home that are consistent in terms of duration and frequency of traversing. FIG. 3 illustrates the process by which paths 14 having the most consistent duration data for use as reference travel time ($T_r$) are established, ranked, and stored, and is represented generally by reference numeral 52. Data from the various sensors 16, 34 and 36 deployed at various locations within the home 12 are collected and stored within the database 44, as represented by block 54. The travel period of the resident between the various sensing locations may then be established, as represented by block 56. The various travel paths 14 are then ranked based on a number of parameters, such as, the length of the traversed path, the consistency of the travel times, and, the frequency of traveling those paths, as represented by block 58. The ranking of the various traveled paths 14 will become better understood in the following description. Finally, the travel paths 14, their corresponding durations, frequency of traveling those paths, and their ranks are stored into the database 44, shown in FIG. 1, as represented by block 60.

Referring to FIG. 4 through FIG. 6, a table listing examples of durations for traversing various paths 14 through the home is illustrated, and is represented generally by reference numeral 62. The table 62 includes a column 64 listing the travel durations for each instance in which the resident took to travel a particular travel path through the home. Each of the travel paths 14 is listed in a column 66. Each travel path 14 corresponds to the sequence of sensors triggered along that path. In this example, the residence has eleven sensors, each having a corresponding number from 1-11 associated with the sensor. Any number of sensors may however be used. A column 68 also is provided to indicate the number of times that each path 14 was traveled over a defined time period.

In this example, each row of the table 62 corresponds to a travel path. The first travel path in the table, represented generally by reference numeral 70, is represented by the triggering of sensors 1, 2, 5, 6, 9, 11, and 7, in that order, as the resident travels along a travel path thorough the home. In this example, the resident has traveled the first path in approximately the same duration each time the resident has traveled along the path. The second travel path provided in the second row of table 62, and represented generally by reference numeral 72, includes walking through the home to trigger sensors 1, 2, 3, 4, 5, 7, 8, and 9, in that order. In the second travel path 72, the travel duration ranges between 7 minutes and 2 seconds to 7 minutes and 10 seconds. As illustrated, the frequency of traveling the second path 72 is higher than the first travel path 70.

A third travel path is provided in table 62, and is represented generally by reference numeral 74. The third travel path 74 is represented by triggering sensors 1, 3, 7, 9, 10, and 11 in a sequence as the resident walks around the home. In the example, the third travel path 74 was traversed twenty-two times over the defined time period. The durations for the travel path 74 range generally from 9 minutes and 6 seconds to 9 minutes and 22 seconds. However, the travel duration is as high as 17 minutes and 6 seconds in one instance, as represented by reference numeral 76. This value is probably not the true travel time. The longer duration of 17 minutes and 6 seconds relative to the other durations may be indicative of the resident stopping mid-way for some activity, such as changing clothes. Therefore, such data may be discarded. A fourth travel path that actuates sensors 2, 4, 5, and 7 in a sequence is provided in table 62 and represented generally by reference numeral 78. As has been illustrated, the travel path 78 was traversed twenty-six times in the given month. However, the resident exhibits a high amount of variation with respect to travel duration for that path. Although the resident generally traverses the fourth travel path 78 in from 3 minutes and 2 seconds to 3 minutes and 29 seconds, there are instances when the resident traverses the path in 2 minutes and 46 seconds, or 10 minutes and 10 seconds.

The travel paths may be ranked based on the consistency of the data and the frequency of the data. For example, the first travel path 70 may have the most consistent data, but because it is traveled so infrequently it may be ranked lower than other travel paths. Conversely, the fourth travel path 78 may be the most frequently traveled travel path, but be ranked lower because its data is less consistent. The length of the travel path may also be a criterion for ranking the travel paths. For example, the longer the distance that a person walks along a path, the more likely it is that the path will be reflective of the person's actual walking speed. Therefore, it may be ranked higher than a shorter travel path with the same frequency and statistically consistent data.

Figure 7:
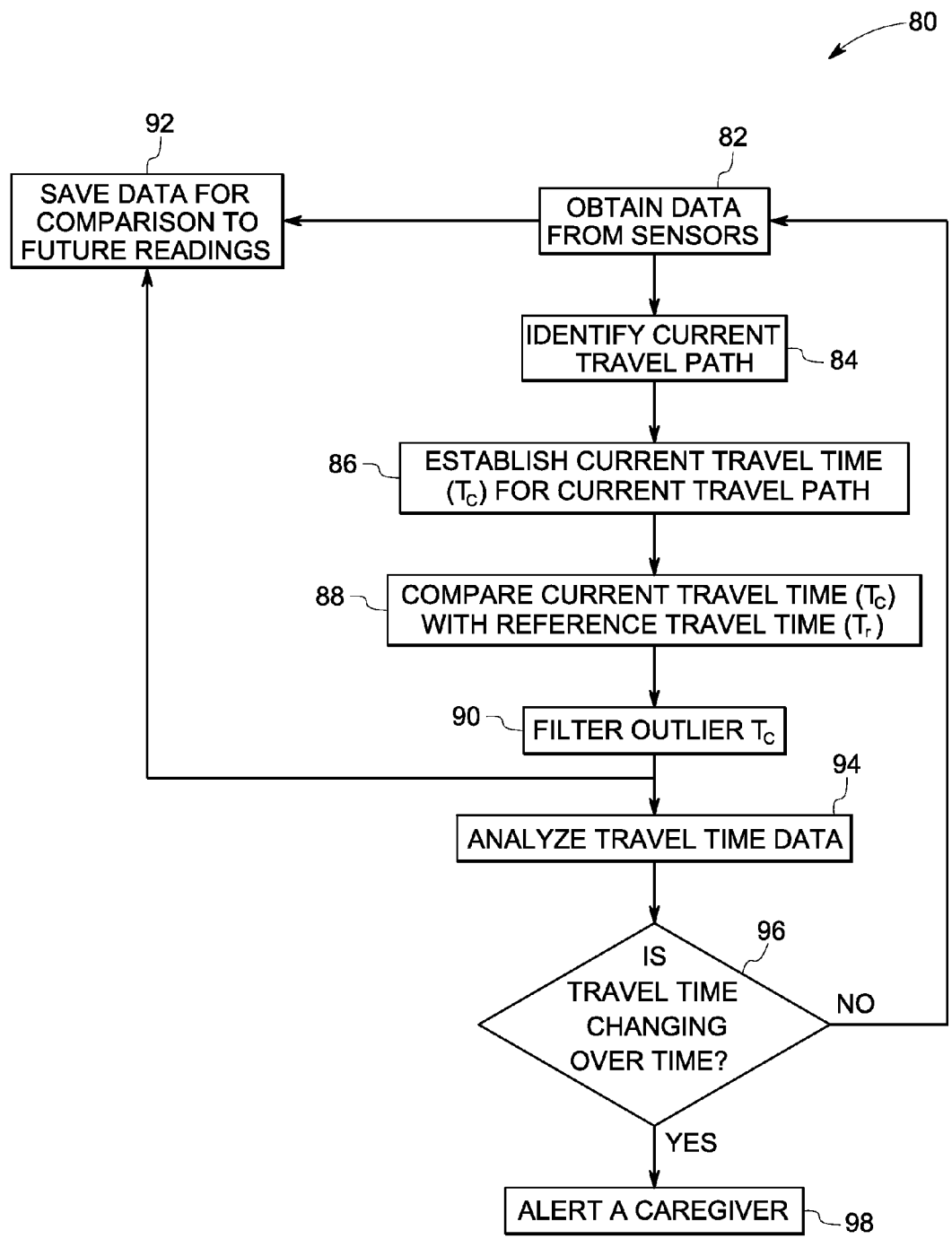
FIG. 7 is a flow chart illustrating an exemplary method for establishing and reporting changes in walking speed, in accordance with one aspect of the present technique.

Referring generally to FIG. 7, an embodiment of a process by which the system 10 monitors the walking speed of a resident over time is illustrated, and is represented generally by reference numeral 80. In the illustrated embodiment, the processor 40 registers activation events transmitted by various sensors that represent movements/activities of the resident along a path, as represented by block 82. The current travel path of the resident is identified, as represented by block 84, and the current travel time ($T_c$) for that path is established by utilizing temporal data 50 corresponding to the movements/activities of the resident, as represented by block 86. It may be noted that identification of the travel path is determined by the sequence that the sensors are triggered.

The current travel time ($T_c$) is then compared with a reference travel time ($T_r$) for the path between the various sensors, as represented by block 88. The reference travel time ($T_r$) may be a single value such as a percentile or maximum value. Alternatively, the reference travel time ($T_r$) may be a distribution representing historical data. Normal distributions may be utilized and may be represented as mean and standard deviations. However, other distributions may also be used. The reference travel time ($T_r$) may adapt to reflect the behavior of the resident and may be updated with respect to each site, or location whenever new measurements are captured.

The current travel time ($T_c$) may be compared with the reference travel time ($T_r$) by simple relational operators when using a single value for reference travel time ($T_r$). Alternatively, current travel time ($T_c$) may be compared with a reference travel time range, by determining if reference travel time ($T_r$) falls within the limits of the normal distribution, such as within a range bound by a multiple of standard deviation of the mean for a normal distribution. In other words, reference travel time ($T_r$) may be compared against 'n' times standard deviation, where 'n' represents the resolution that the caregiver requires for determining the limits for the range of reference travel time ($T_r$). A lesser value of 'n' gives a more compact range. One skilled in the art will recognize that many different comparison techniques may be utilized. If the current travel time ($T_c$) is much greater or smaller than the reference travel time ($T_r$), such that the difference ($T_c-T_r$) is larger than a predefined value, the processor 40 will disregard the data, as represented by block 90, because such travel times ($T_c$) are outliers that are not indicative of the true walking speed of the resident. For example, if the resident stops along the way, the current travel time ($T_c$) will be much greater than what the reference travel time ($T_r$) should be. One example of such a travel time is the travel time represented by reference numeral 76 in FIG. 4. The value (i.e. $T_c-T_r$) that is chosen as the threshold to disregard the current travel time ($T_c$) is preferably selected so that only data that is truly not representative of the walking speed of the resident is disregarded.

Other current travel times ($T_c$) that are truly representative of the walking speed of the resident are stored in the database 44 and may be used to establish a new or initial value for the reference travel time ($T_r$), as represented by block 92. Such current travel times ($T_c$) are used to analyze the walking speed of the resident over time, as represented by block 94. The analysis is performed to establish if the travel time is changing over time, as represented by block 96. If the travel time of the resident shows a consistent increase or decrease over time, this is indicative that the walking speed of the resident is changing and an alert may be sent automatically to a caregiver, as represented by block 98. Other actions may be taken, such as telephoning the resident to inquire into the resident's health. When completed, the current travel time ($T_c$) is stored in the database 44 and may be used to establish a new or an initial value for the reference travel time ($T_r$).

Alternatively, the data may be examined using older data, such as data that is representative of the walking speed a week or a month earlier, with more recent data and comparing the values. For example, when the durations are represented as normal distributions, then the means and standard deviations can be compared to determine if they are statistically different and if indeed the duration to travel the path is changing. However, if the travel duration for the various paths that the resident traverses does not change significantly, the system will continue to update itself with the sensor data and monitor the walking speed to determine changes.

Furthermore, if there is a significant decrease in travel time, for a single event, while traversing the staircase 30, this may be evidence that the resident has fallen down the staircase 30. Therefore, the sensor data may be prioritized according to the location of the sensor and the processor may be allowed to initiate alarms/alerts accordingly. The caregiver may be alerted by an electronic mail service or an electronic text message system, such as on a cell phone or a pager. Similarly, other methods of alerting the caregiver may also be utilized, such as a visual alert, an audible alert, a tele-textual signal, or the like may be utilized. The caregiver may then attend to the resident in such cases. Alternatively, a significant increase in the duration of walking along several paths in one day may be an indication that the resident has experienced a sudden severe health problem. The monitoring center 18 may then alert the caregiver, or resident.

In another embodiment, patterns, where variation in the duration of the patterns may be smaller than the expected changes in the durations, may also be established in accordance with aspects of the same technique. For example, when the resident covers the path through the staircase 30 with sensors installed at the top and bottom of the staircase 30, the resident may take approximately the same amount of time to go up the staircase every time, for example about 30 seconds. Then, if the resident starts taking 50% longer time (for example around 45 seconds) to climb the staircase 30 because they are frequently out of breath, the system can detect the change in the walking speed. However, if the shift is low, such as only 1% (30.3 seconds), the monitoring center 18 may not actuate or initiate an alert to the caregiver. It may be borne that each direction of travel of the staircase is a separate path since the order each of the sensors activate may be utilized to distinguish between the paths.

Similarly, it will be appreciated by those skilled in the art that the methods and algorithms described hereinabove may be utilized to see if the resident's walking speed has increased. For example, it may be expected that a medication taken by the resident would improve the health of the resident. This improvement may be manifested by an increase in the resident's walking speed over a period of time, which would result in shorter travel times. For example, if the resident is recovering from a bypass surgery, the recovery may be manifested by an improved walking speed of the resident. The methods and algorithms described hereinabove may be utilized to monitor the improvement in walking speed and therefore the progress in recovery over a number of days, weeks or months. Thus, such statistical walking speed data may be used as a prognostic tool.

It will be appreciated by those skilled in the art that the methods and algorithms described hereinabove may be embedded in a dedicated processor such as an ASIC (application specific integrated circuit) or, a digital signal processor configured for processing the signals. Alternatively, computer readable instructions may be embedded in the processor 40 of the monitoring center 18 to process the above mentioned sensor data.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method of operating a monitoring system to identify a change in walking speed of a person, comprising:
   receiving data representative of movement of the person within a structure and the time that the movement occurred;
   processing the data to establish a representative travel time for the person to walk along a specific sequence of sensors from among a plurality of different sequences of sensors; and
   periodically comparing a current travel time for the person to walk along the specific sequence of sensors to the representative travel time to identify a change in the travel time for the person to walk along the specific sequence of sensors.

2. The method as recited in claim 1, wherein receiving data representative of movement of the person comprises receiving data from a plurality of motion sensors operable to detect movement of the person in a location within the structure.

3. The method as recited in claim 1, wherein receiving data representative of movement of the person comprises receiving data from at least one occupancy sensor operable to detect when the person is positioned on the at least one occupancy sensor within the structure.

4. The method as recited in claim 1, wherein receiving data representative of movement of the person comprises receiving a signal representative of one of a door being open or closed.

5. The method as recited in claim 1, wherein processing the data comprises establishing travel times for the person to walk along the plurality of sequences of sensors and identifying those specific sequences of sensors of the plurality of sequences of sensors having generally consistent travel times and wherein the representative travel time comprises a representative travel time for one of the specific sequences of sensors having generally consistent travel times.

6. The method as recited in claim 1, comprising contacting a caregiver when a changing trend in the travel time between the sequences of sensors is identified.

7. A method of operating a monitoring system to identify a change in walking speed of a person, comprising:
receiving a signal representative of movement of the person from each of a plurality of sensors disposed within a building;
establishing travel times for walks that the person takes between rooms of the building based on the signals representative of movement of the person received from the plurality of sensors disposed within the building;
identifying at least one path through a first plurality of rooms in the building that produces consistent travel times from among a plurality of paths through a plurality of rooms in the building; and
storing a representative travel time of a walk along the path through the first plurality of rooms as a reference for comparison over time.

8. The method as recited in claim 7, wherein receiving a signal representative of movement of the person comprises receiving a signal representative of location of the person within the building.

9. The method as recited in claim 7, comprising periodically comparing a current travel time for a walk along the path through the first plurality of rooms with the representative travel time.

10. The method as recited in claim 9, comprising notifying a caregiver if the current travel times are changing over time.

11. A non-transitory computer readable medium that stores programming instructions executable by at least one processor-based device, wherein the programming instructions enable the processor-based device to establish travel times for a person walking between rooms of a building based on data received from a plurality of sensors in the building and the programming instructions enable the processor-based device to identify a specific sequence of rooms that are walked through by the person as producing the consistent travel times.

12. The non-transitory computer readable medium as recited in claim 11, wherein the programming instructions enable the processor-based device to establish a representative travel time for the specific sequence of rooms that are walked through by the person as producing consistent travel times.

13. The non-transitory computer readable medium as recited in claim 12, wherein the programming instructions enable the processor-based device to compare travel times with the representative travel time to identify a trend towards a change in the travel times.

* * * * *